United States Patent [19]

Steenhoek

[11] Patent Number: 4,917,495
[45] Date of Patent: Apr. 17, 1990

[54] PORTABLE COLORIMETER AND METHOD FOR CHARACTERIZATION OF A COLORED SURFACE

[75] Inventor: Larry E. Steenhoek, Wilmington, Del.

[73] Assignee: E. I. Du Pont de Nemours and Company, Wilmington, Del.

[21] Appl. No.: 286,785

[22] Filed: Dec. 20, 1988

[51] Int. Cl.$^4$ .............................. G01J 3/18; G01J 3/50
[52] U.S. Cl. ..................... 356/328; 356/405; 356/446; 364/526
[58] Field of Search ............... 356/326, 328, 405, 406, 356/407, 446; 250/226; 364/526

[56] References Cited

U.S. PATENT DOCUMENTS

| | | | |
|---|---|---|---|
| 3,389,265 | 6/1968 | Schreckendgust | 250/226 |
| 3,690,771 | 9/1972 | Armstrong, Jr. et al. | 356/405 |
| 3,885,878 | 5/1975 | Ishak | 356/405 |
| 3,916,168 | 10/1975 | McCarty et al. | 235/151.3 |
| 3,999,864 | 12/1976 | Mutter | 356/448 |
| 4,449,821 | 5/1984 | Lee | 356/319 |
| 4,479,718 | 10/1984 | Alman | 356/405 |
| 4,583,858 | 4/1986 | Lebling et al. | 356/402 |
| 4,669,880 | 6/1987 | Nelson et al. | 356/326 |
| 4,711,580 | 12/1987 | Venable | 356/406 |

*Primary Examiner*—F. L. Evans
*Attorney, Agent, or Firm*—Hilmar L. Fricke

[57] ABSTRACT

A portable colorimeter for characterizing the optical properties of a colored surface and in particular a colored surface containing metallic or pearlescent particles, which employs three multiangular spectrophotometric measurements to derive color constants for the surface. The colorimeter is a compact integrated unit housing irradiation, detection, control, analysis and display means and employs three illumination angles, preferably $-30°$, $0°$, and $65°$, and one detection angle, preferably $45°$, all measured from the sample normal. The method includes determining the tristimulus values of the color of the sample surface from low resolution spectral reflectance data preferably using twelve detector elements.

21 Claims, 8 Drawing Sheets

PORTABLE COLORIMETER AND METHOD FOR CHARACTERIZATION OF A COLORED SURFACE

BACKGROUND OF THE INVENTION

This invention is directed to a portable colorimeter and a method for the characterization of a colored surface and in particular a color surface containing metallic or pearlescent particles.

In the manufacture of pigmented finishes one rarely, if ever, achieves a satisfactory color match versus a color standard without an adjustment process known as shading. Shading usually involves a relatively minor but critical manipulation of the formula pigment composition, correcting for the cumulative effects of manufacturing variables on pigment dispersions.

Traditionally, the shading process has been carried out by highly skilled and trained personnel who require extensive on-the-job experience to achieve proficiency in their craft. Since visual shading at best is an art, effective administration of the process was difficult.

In more recent years, such visual shading has been supplemented by the use of apparatuses for instrumentally characterizing a paint or pigment composition. Colorimeters and spectrophotometers are well-known in the art and are used to measure certain optical properties of various paint films which have been coated over test panels. A typical spectrophotometer provides for the measurement of the amount of light reflected at varying light wavelength in the visible spectrum by a painted panel that is held at a given angle relative to the direction of an incident source of light. The reflectance factor of the paint enables paint chemists to calculate color values by which to characterize various paint colors. For a paint containing no light-reflecting flakes or platelets (i.e., non-metallic paints), the reflectance factor will not vary with the angle of the panel relative to the direction of incident light except at the gloss (specular) angle. Consequently, a single spectrophotometric reading at any specified angle will produce a reflectance value by which to accurately characterize the paint.

However, the paint industry often utilizes light-reflecting flakes in paints (i.e., metallic paints) to obtain pleasing aesthetic effects. Paints containing light-reflecting flakes of such materials as aluminum, bronze, coated mica and the like are characterized by a "two-tone" or "flip-flop" effect whereby the apparent color of the paint changes at different viewing angles. This effect is due to the orientation of the flakes in the paint film. Since the color of such metallic paints will apparently vary as a function of the angle of illumination and viewing, a single spectrophotometric reading is inadequate to accurately characterize the paint. Although measurement studies have shown that visual color differences existing between two metallic paints were detectable at an infinite number of angles, it is obvious that practical reasons preclude the collection of reflectance factors for an infinite number of viewing angles. However, previous studies have also indicated that measurement of the optical properties of a metallic paint at only two or three specified angles can provide useful characterization. See, for example, U.S. Pat. No. 3,690,771, issued Sept. 12, 1972 to Armstrong, Jr., et al and U.S. Pat. No. 4,479,718, issued Oct. 30, 1984 to Alman, the disclosures of which are incorporated herein by reference.

Instruments have also been devised wherein measurements are taken at a fixed angle by varying the angles of illumination. See, for example, U.S. Pat. No. 4,583,858, issued Apr. 22, 1986 to Leblin et al. Various other devices and methods are disclosed in U.S. Pat. Nos. 3,389,265; 3,885,878; 3,916,168; 3,999,864; 4,449,821; 4,669,880; 4,711,580.

However, there is a need in the automobile paint industry for a device which is portable, compact, and capable of measuring the color of automobile panels and the like, and especially metallic or pearlescent finishes.

OBJECTS AND SUMMARY OF THE INVENTION

The principal object of the present invention is to provide a portable colorimeter for characterizing the optical properties of a color surface and in particular a colored surface containing metallic or pearlescent particles by using three multiangular spectrophotometric measurements to derive color constants for the sample surface.

An object of the present invention is to provide a portable colorimeter which includes a compact integrated unit for housing irradiation, detection, control, analysis, and display means.

Another object of the present invention is to provide a portable colorimeter which employs three illumination angles preferably of $-30°$, $0°$, and $65°$, and one detection angle preferably of $45°$, as measured from the sample normal.

Yet another object of the present invention is to provide a portable colorimeter which employs a silicon photo diode array detector comprising 10–16 detector elements for detection across the entire visible spectrum.

An additional object of the present invention is to provide a method for characterizing the optical properties of a surface containing metallic or pearlescent flakes by determining the tristimulus values (color constants X, Y, Z) from low resolution spectral reflectance data by correcting the tristimulus function curve representing sensitivity data of the human eye by multiplying it with the spectral power distribution curve of the illuminant, determining the spectral response curve of the detector elements represented as a series of generally triangular pass bands, and fitting the illuminant corrected tristimulus function curves with a multiple linear combination of the triangular pass bands representing the spectral response curve.

In summary, the main object of the present invention is to provide a portable compact colorimeter and a method for characterizing a colored surface in particular a colored surface containing metallic or pearlescent particles, which employs three illumination angles and one detection angle.

DETAILED DESCRIPTION OF THE INVENTION

Figure 1:
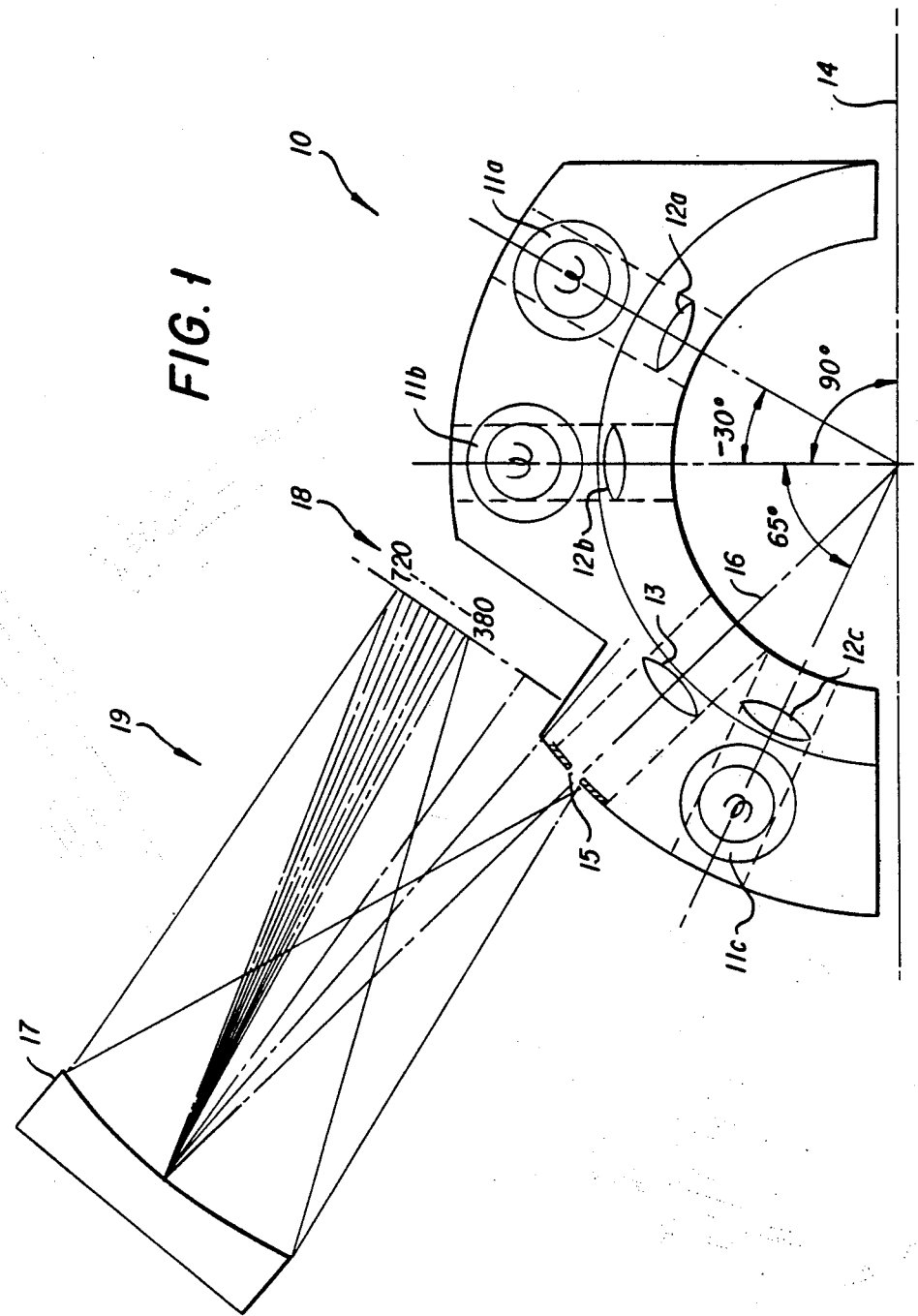
FIG. 1 is a schematic illustration of the portable colorimeter of the present invention.

In optically characterizing surfaces containing metallic particles, such as metallic paints and films, it was recognized that directional reflectance had to be considered. Metallic paints contain light-reflecting flakes or platelets of such material as aluminum, bronze, coated mica and the like. These flakes or platelets function much like little mirrors, reflecting light directionally rather than in a diffuse manner. The directional reflectance characteristic of a metallic paint film results in a phenomenon known as goniochromatism, which is defined as the variation in color of a paint film as a function of the directions of illumination and viewing. This phenomenon is also sometimes described as "two-tone", "flop" "flip-flop", "flash", "side-tone", etc. In sum, the color of a metallic paint will appear different at different viewing and/or illumination angles.

To account for this directional or angular reflectance, i.e., goniochromatism, spectrophotometrically determined reflectance factors must be taken multiangularly. The reflectance factor of a paint film is the ratio of the light flux reflected from the film sample to the light flux reflected from a perfect reflecting diffuser when the sample and perfect diffuser are identically irradiated. A perfect white reflector has a value of 1. A perfect black nonreflector has a value of 0.

The reflectance factors are used to calculate color descriptor values used to specify color and color difference. The tristimulus values (X, Y, Z) of a color are calculated by combining the reflectance factor data (R) with data on the sensitivity of the human eye ($\bar{x}, \bar{y}, \bar{z}$) and the irradiance of a light source (E) all as functions of wavelength ($\lambda$) in the visible spectrum. The defining equations for tristimulus values are:

$$X = \int_{360}^{830} R(\lambda)E(\lambda)x(\lambda)d\lambda$$

$$Y = \int_{360}^{830} R(\lambda)E(\lambda)y(\lambda)d\lambda$$

$$Z = \int_{360}^{830} R(\lambda)E(\lambda)z(\lambda)d\lambda$$

The tristimulus values can be used to calculate color descriptors which relate to visual perception of color and color difference. One of many sets of descriptors which can be used is the CIELAB perceptual color scale recommended by the International Commission on Illumination ("Recommendations on Uniform Color Spaces, Color Difference Equations, Psychometric Color Terms", Supplement No. 2 To CIE Publication No. 15 (E1.3.1) 1971/CT(1.3) 1978. Bureau Central De La CIE, 52 Boulevard Malesherbes 75008, Paris, France).

Transformations of the tristimulus values can be used to calculate perceptual color values describing lightness ($L^*$), redness/greenness ($a^*$), yellowness/blueness ($b^*$), saturation (C) or hue (h). A color can be completely described by a set of L, a, b or L, C, h values. The following equations which have been specified by the International Committee on Illumination relate the tristimulus values to $L^*$, $a^*$ and $b^*$ $$L^* = 116(Y/Y_o)^{\frac{1}{3}} - 16$$

$$a^* = 500[(X/X_o)^{\frac{1}{3}} - (Y/Y_o)^{\frac{1}{3}}]$$

$$b^* = 200[(Y/Y_o)^{\frac{1}{3}} - (Z/Z_o)^{\frac{1}{3}}]$$

where $X_o$, $Y_o$ and $Z_o$ are the tristimulus values of the perfect white for a given illuminant;

X, Y and Z are the tristimulus values for the color.

The saturation (C) and hue (h) descriptors are related to the $a^*$ and $b^*$ values as follows:

$$C = (a^{*2} + b^{*2})^{\frac{1}{2}}$$

$$h = \tan^{-1}(b^*/a^*)$$

Often it is necessary to compare a color, such as a sample batch of paint, to a standard color and determine the difference and then adjust the sample with appropriate additives to bring the sample within tolerance values of the standard. The difference in color between a color standard and a batch sample is described as follows:

$$\Delta L^* = L^* (\text{batch}) - L^* (\text{standard})$$

$$\Delta a^* = a^* (\text{batch}) - a^* (\text{standard})$$

$$\Delta b^* = b^* (\text{batch}) - b^* (\text{standard})$$

The resultant values agree with the visual assessments of differences in lightness ($\Delta L^*$), redness/greenness ($\Delta a^*$) and yellowness/blueness ($\Delta b^*$).

Further discussion will employ the tristimulus values (X, Y, Z) and perceptual color values ($L^*$, $a^*$, $b^*$, C, h) to quantify the influence of changing conditions of illumination and viewing on measurement of goniochromatic color. The specific color descriptors employed are only one of many possible choices of transformations of tristimulus values which could be employed in this task.

The method used in the portable three angle colorimeter of this invention to calculate color constants X, Y, Z of a sample is different from that used in conventional filter colorimeters or spectrophotometers.

Filter colorimeters utilize optical filters whose transmission spectra have been tailored such that the product of the spectral power distribution curve of the light source, the filter transmittance curve and the detector spectral response curve closely approximate the tristimulus response functions ($\bar{x}, \bar{y}, \bar{z}$ response of the human eye) for a given illuminant. The signal from each of three detectors (red, yellow-green, and blue) relative to a white standard gives a direct measurement of the color coordinates of a sample. To measure color under a different illuminant would require a different set of filters. (See, for example, U.S. Pat. No. 4,711,581 to Venable).

Conventional spectrophotometers measure the reflectance of the sample at a series of evenly spaced non-overlapping intervals (typically 10 nm) across the visible portion of the optical spectrum. These reflectance values are then multiplied point by point by the tristimulus response functions ($\bar{x}, \bar{y}, \bar{z}$) corrected for the illuminant and/or observer of choice. Properly normalized the sum of these products yield the color coordinates for the sample. In typical spectrophotometers anywhere from 16 to 31 detectors are employed for the point by point measurement of the visible spectrum. Description of such conventional measurement can be found in Publication CIE No. 15 (E-1.3.1) 1971, COLORIMETRY.

In the method employed by the portable colorimeter described below, however, the sample reflectance spectrum is determined, preferably by using only twelve detector elements. The spectral sensitivity or response of each of the twelve detector elements is described by a generally triangular shape pass band which is a representation of the shape of the intensity envelope with respect to wavelength location The illuminant corrected tristimulus function curve is then fit by a multiple linear combination of these triangular shape pass bands which when properly normalized yields color constants, i.e., tristimulus values X, Y, Z.

Relying on a conventional principle that three properly selected measurement angles are an optimized selection to give maximum information on metallic color for minimum measurement effort, a portable instrument has been constructed. However, in order to minimize space requirements, the portable three angle colorimeter employs a reverse geometry. The conventional method used multiangular spectrophotometric measurements taken at three specified angles, preferably 15°, 45°, and 110° as measured from the specular angle, with a single light source having an illumination angle of 45° relative to the metallic paint sample being measured (which is the same as saying the light reflected is detected at −30°, 0°, and 65° as measured from the sample normal).

However, in the portable colorimeter of this invention, multiple light sources sequentially illuminate the sample at angles of about −35° to −20°, 10° to +10° and 20° to 75°, preferably from −30°, 0°, and 65° as measured from the sample normal, and light reflected from the sample is detected at a detection angle from about 35°-55°, preferably at 45°, as measured from the sample normal.

In addition, the portable instrument of this invention employs a different method for determining the tristimulus values X, Y, Z, of a paint sample by using low resolution spectral data obtained from a silicon photo diode array detector, preferably comprising only twelve elements for detection across the entire visible spectrum (380 nm–700 nm). By this method, the illuminant corrected tristimulus function curve is fit with a multiple linear combination of the triangular pass bands for each of the twelve elements.

COLORIMETER

As schematically shown in FIG. 1, the portable colorimeter 10 of this invention employs three sources of illumination, lamps 11a, 11b, and 11c. The output of these lamps is collimated by each achromatic source lens 12a, 12b, and 12c mounted at its focal length form the lamp filament. Each lamp may be a 20 watt quartz halogen lamp, such as the lamp manufactured by Gilway Technical Lamp, Model Number L7404. In order for the measurement technique employed in this device to work properly it is necessary that the lamps operate at a fixed color temperature as will be discussed below. The lenses employed may be Model Number 01-LAU004-006, manufactured by Melles Griot.

The collection optics may include a single achromatic collection lens 13 (Melles Griot 01LAU006-006) mounted at twice its focal length from the sample surface 14. A monochromator 19, comprising a diffraction grating 17 and a silicon diode array detector 18 is mounted opposite to the sample side of lens 13. Entrance slit 15 to monochromator 19 is mounted at a distance of one focal length from lens 13. This arrangement permits only light 16 which is very nearly collimated to pass through entrance slit 15 permitting only light scattered at or about 45° from the sample normal to enter the monochromator 19.

After passing through entrance slit 15, light 16 diverges until it hits the diffraction grating 17 where it is dispersed and refocused onto a silicon diode array detector 18 with twelve detecting elements 21. The diffraction grating 17 may be Model No. 523-00-460 as manufactured by Instruments SA. The array detector 18 may be Model No. LD20-5, as manufactured by Centronics. Preferably, the dimensions of the entrance slit are 0.9 mm × 4.0 mm.

Figure 2:
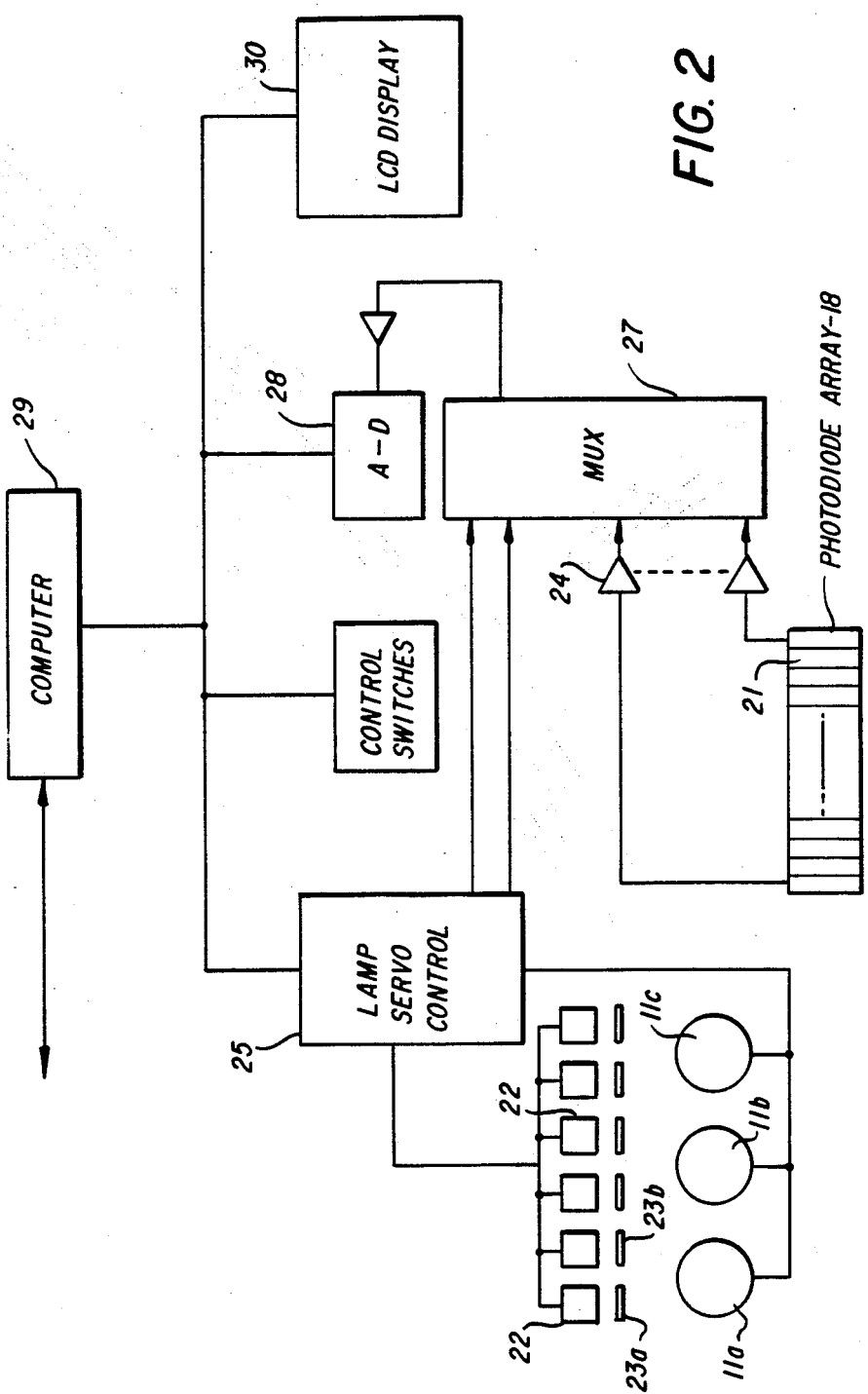
FIG. 2 is a schematic for the control circuitry of the colorimeter.

The visible spectrum of light 16 is dispersed and refocused across array detector 18. As schematically shown in FIG. 2, each of the elements 21 of the photodiode array detector 18 has an associated amplifier 24 which converts the diode current to a voltage signal. The twelve signals are then multiplexed by multiplexer 27 and digitized by an analog to digital converter 28. The amplifier may be Model No. OPA2111 as manufactured by Burr-Brown. The multiplexer 27 may be Model Number AD7506KN as Manufactured by Analog Devices. The analog to digital converter may be Model No. ADC71JG as manufactured by Burr-Brown.

All of the functions are controlled by microcomputer 29, which may be an INTEL 8052 based computer with auxiliary I/O and memory card. The measurement data as will be described below derived from the portable instrument is displayed on an LCD display 30.

As can be seen by FIG. 1, in portable colorimeter 10, the sample is sequentially illuminated, preferably from −30°, 0°, and 65° as measured from the sample normal. Light reflected from the sample is detected, preferably at 45° as measured from the sample normal. It should be noted that the illumination and detection angles may be varied and the specific angles provided herein are merely optimum values.

As mentioned above, for proper operation of the colorimeter, the illumination source lamps 11a, 11b, and 11c operate at a fixed color temperature. Since the lamps are turned on only for a few seconds each per measurement, time is insufficient to allow the lamps to "warm up" to equilibrium in order to achieve consistent color-temperature. Thus the lamps, as schematically shown in FIG. 2, are controlled by an active feedback circuit. Each source lamp 11a, 11b, and 11c is monitored by two photodiodes 22. A blue filter 23a is placed in front of one photodiode and a red filter 23b is placed in front of the other. Each of these diodes produces a voltage signal which is proportional to the lamp emission in the blue and red regions of the spectrum, respectively. The control circuit as schematically designated by block 25, adjusts the lamp current to maintain a fixed ratio between the output voltages of the two diodes, thus maintaining a fixed color temperature.

Figure 3:
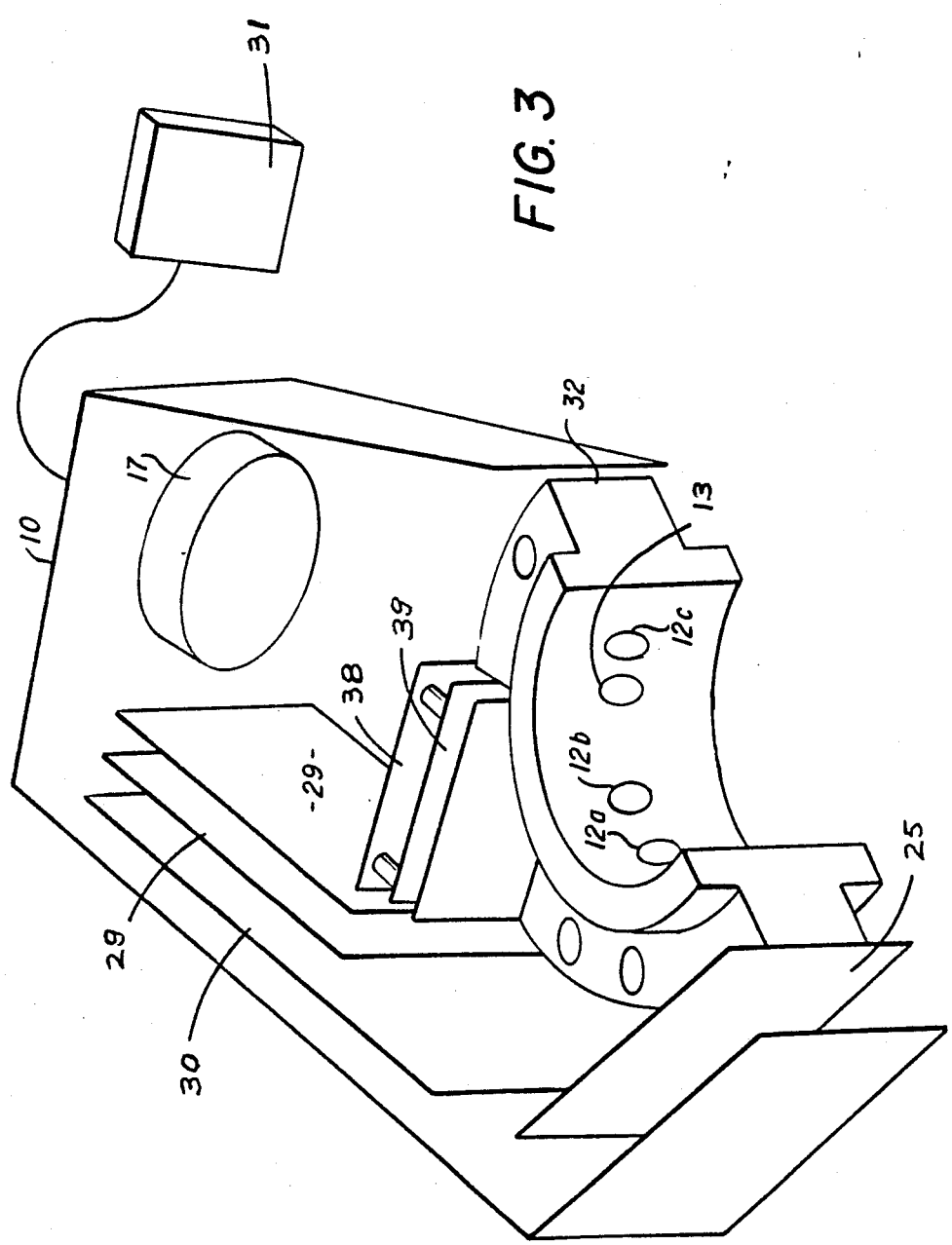
FIG. 3 is a perspective partial view of the colorimeter showing the necessary parts only.

FIG. 3 shows a plan view of the interior of portable colorimeter 10, illustrating only the parts necessary for an understanding of the invention. Schematically shown is the layout of the illumination sources as represented by illumination lenses 12a, 12b, and 12c; collection lens 13; lamp control circuit 25; card 38 which comprises multiplexer 27 and analog to digital converter 28; detector card 39 which comprises elements of photodiode array 21 and amplifier 24; computer control and analysis means 29; diffraction grating 17; and LCD display 30. The instrument may be powered by a remote battery pack 31 which may be shoulder mounted by an operator. Preferably, the instrument is of the approximate size $3\frac{1}{2}'' \times 8'' \times 10''$, approximate weight of 7 lbs, and has a flat measuring surface of approximately two inches.

Figure 4:
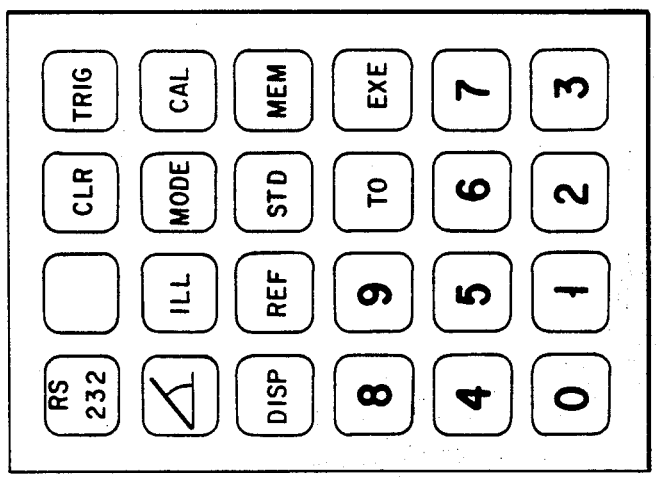
FIG. 4 is a representation of the operator key pad.
Figure 5:
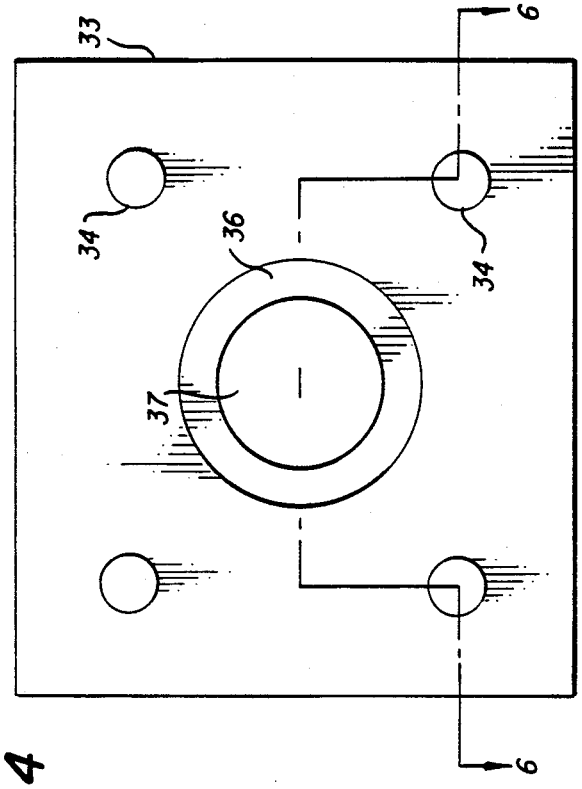
FIG. 5 is an illustration of the measuring surface of the colorimeter.
Figure 7:
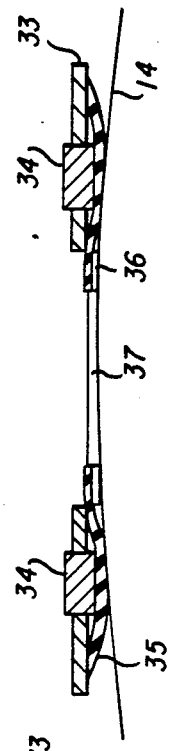
FIG. 7 is an illustration of the measuring surface resting on the color sample.
Figure 6:
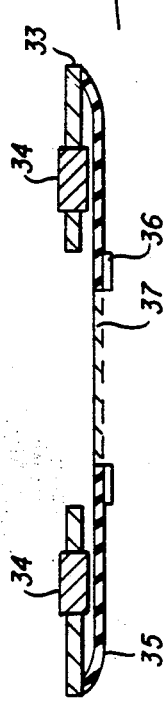
FIG. 6 is a view taken along line 6—6 of FIG. 5.

An interface plate 33 mounts over the lenses 12a, 12b, 12c, and 13, and is affixed to mounting block 32 (FIG. 5). Referring to FIG. 7, four magnetic feet 34 protrude through interface plate 33. Each foot 34 is a rare earth magnet which is covered with neoprene sheeting 35 of approximately 1/16" thickness. The feet may be circular disc magnets of Sm/Co of approximately $\frac{1}{2}''$ diameter and $\frac{3}{8}''$ thickness, such as those manufactured by Crucible Magnetics. The feet 34 provide registration and resistance to slippage to a curved surface of an automobile panel to be measured, and the neoprene sheeting 35 provides protection to the car finish against, for example, surface scratching. In the center of the interface plate 33 is a donut shaped flexible magnet 36 which provides a light tight seal around measurement port 37. The spacing of the magnetic feet 34 and the distance that feet 34 protrude define the minimum radius of curvature of the surface which can be measured, approximately 24 inches. The operator key pad is shown in FIG. 4.

The instrument is provided with an internal temperature monitor (not shown) located near the detector elements 21. Because of the instrument's portability, the temperature of the environment under which the instrument will be expected to operate may vary widely. To insure uniformity of results, temperature parameter limits are determined and preprogramed into the instrumentation. When such limits are exceeded, the operator is alerted and forced to recalibrate the instrumentation. The temperature sensing chip may be an Integrated Circuit Temperature Transducer AD592.

METHOD FOR CALCULATION OF COLOR CONSTANTS

Three factors are essential for the production, perception and measurement of color: The source of light, the illuminated object, and the detector. Each of these three is described, by an appropriate response curve plotted against wavelength: the light source, by its spectral power distribution curve; the object, by its spectral reflectance or transmittance curve; and the detector, by its spectral response curve. The combination of these curves provides the stimulus, or signal, which is represented as the numerical descriptors of color X, Y, Z—the tristimulus values. Thus the tristimulus values (X, Y, Z) of a color are calculated by combining the reflectance factor data (R) with data on the sensitivity of the human eye ($\bar{x}, \bar{y}, \bar{z}$) and the irradiance of a light source (E) all as functions of wavelength ($\lambda$) in the visible spectrum, as described above.

Figure 8:
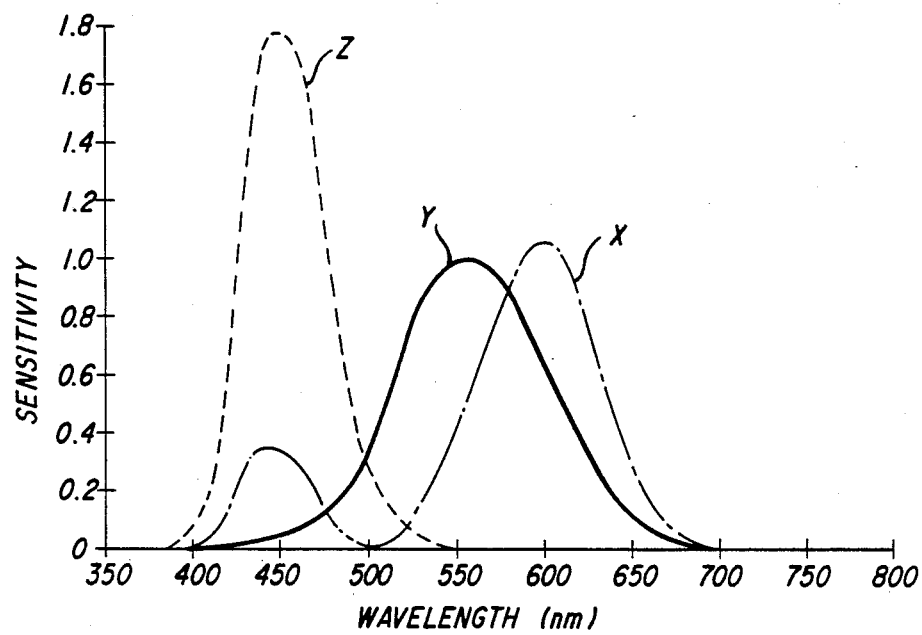
FIG. 8 shows the tristimulus function curves representing the sensitivity data of the human eye.

FIG. 8 shows the tristimulus response functions curves $\bar{x}, \bar{y}, \bar{z}$ as cited in "Principles of Color Technology", page 44, 2nd Edition, Billmeyer and Saltzman, John Wiley & Sons (1981).

Figure 9:
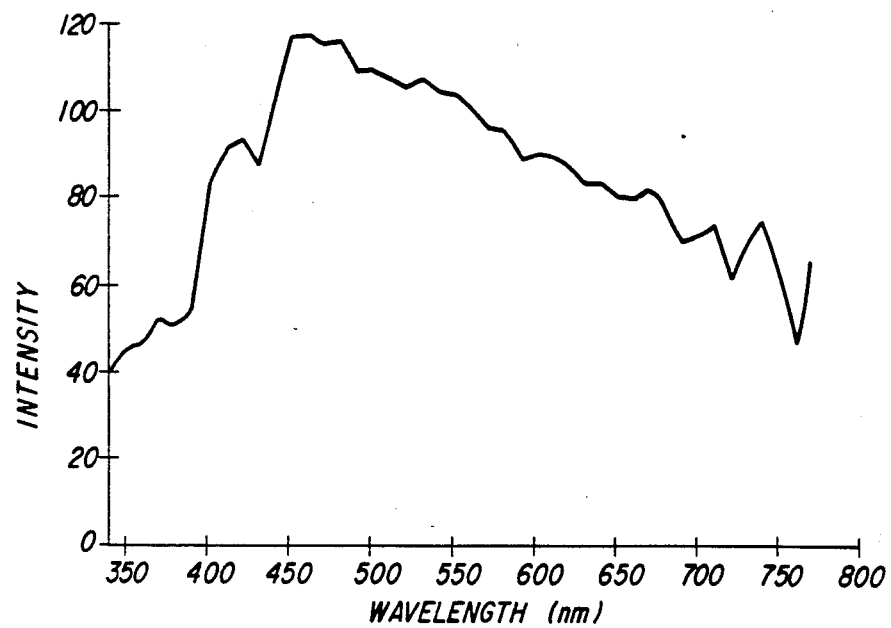
FIG. 9 is the spectral power distribution curve for the illuminant.

FIG. 9 shows the spectral power distribution curve for the illuminant used. In the present embodiment two different standard illuminants are used. FIG. 9 shows the spectral power distribution for CIE Source D65 which is a representation of average natural daylight over the visible spectrum having a correlated color temperature of 6500° K. The other illuminant source is CIE Source A which is a tungsten-filament lamp operating at a color temperature of 2854° K. For most applications of the portable colorimeter, the taking of measurements using these two variant illuminants at the three stated angles should suffice. However, it is well within the scope of this invention to employ other standard illuminants for taking measurements. The values for the spectral power distribution curve shown in FIG. 5, are cited in "Principles of Color Technology", pp. 36–37, 2nd Edition, Billmeyer and Saltzman, John Wiley & Sons (1981).

Figure 10:
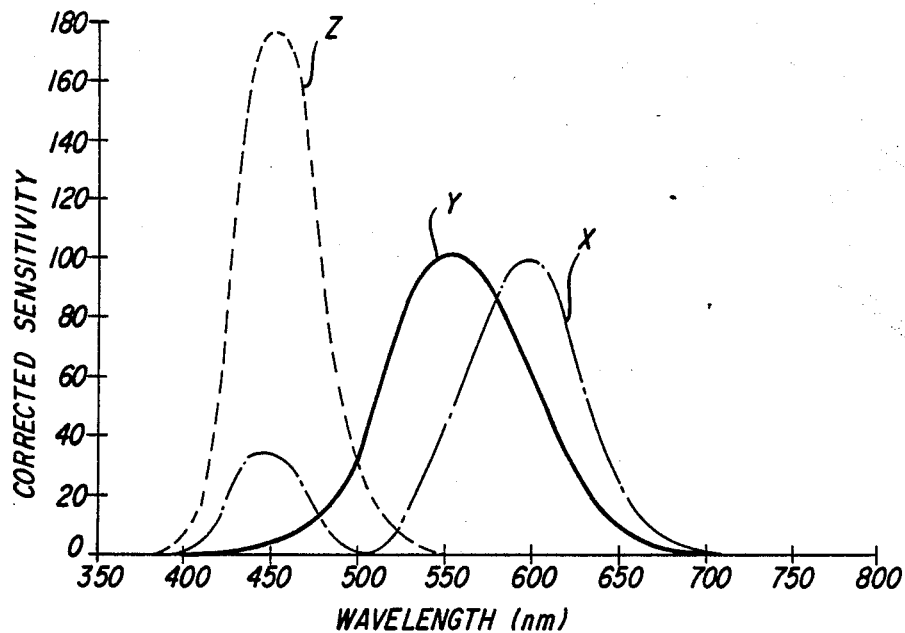
FIG. 10 shows the illuminant corrected tristimulus function curves.

By multiplying the tristimulus response curves (FIG. 8) by the spectral curve for the illuminant (FIG. 9) corrected response curves as shown in FIG. 10, are produced.

Figure 11:
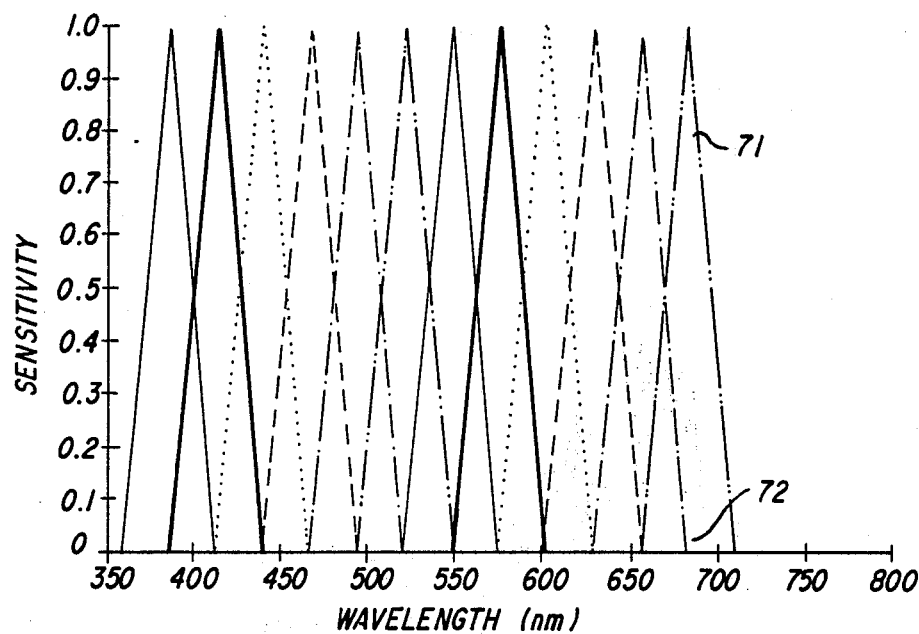
FIG. 11 shows the spectral response curves of the detector elements as represented by a series of triangular pass bands.

FIG. 11 shows the spectral response curves for the detector elements. The diagram represents data from photodiode detector array 18 which may be seen as a series of triangular pass bands 71 whose vertex is associated with wavelength 72. The spectral sensitivity of each of the twelve detector elements 21 is represented by triangular pass band 71 whose base width is equal to the portion of the spectrum subtended by two detector elements, i.e., 56–60 nm. Each of the corrected response curves of FIG. 10 is fit with a multiple linear combination of detector response triangles from FIG. 11. The multiple linear combination used is the same as that cited in "Applied Regression Analysis", page 178, Draper and Smith, John Wiley & Sons, Inc., N.Y. (1966).

Figure 12:
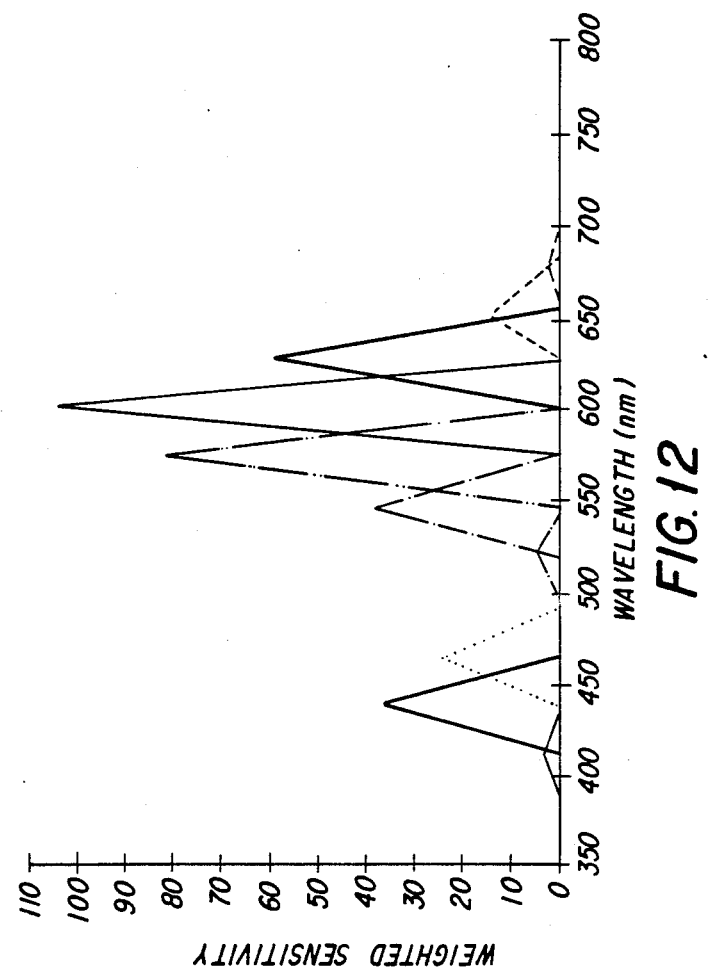
FIG. 12 shows the weighted detector response function curves.

FIG. 12 shows the result of this fit for the $\bar{x}$ tristimulus function of FIG. 8, where each of the triangular pass bands has been weighted by the coefficients derived from the fit. A set of weighting coefficients for each tristimulus function curve and for each illuminant used may be derived. Thus, in the instrument of this invention three sets of weighting coefficients, one for each tristimulus function for illuminant A are derived and three sets of weighting coefficients for illuminant D65 are derived.

In the portable colorimeter 10, color coordinates are calculated in the following manner. The instrument is first zeroed by measuring a black glass tile (not shown). These values are subtracted from any future measurement. Then, the reflectance spectrum of a white calibration tile (not shown) is measured, and a series of gain coefficients is calculated to adjust numerically the response of each detector element 21 to be equal to the reflectance of the calibration tile at the appropriate wavelength. Any subsequent detector readings are multiplied by these gain coefficients.

To measure a sample panel, the colorimeter is first secured on the panel by magnetic feet 34 and lamps 11a, 11b and 11c sequentially illuminate the sample surface at $-30°$, $0°$, and $65°$ as measured from the sample normal. The light reflected from the panel is collected by lens 13 at 45° as measured from the sample normal, and is collimated to pass through entrance slit 15 to enter monochromator 19 (FIG. 1) Once in the monochromator, the collected light is detected by array detector 18 and ultimately converted to a voltage signal. The measurements taken are processed by microcomputer 29 and displayed on LCD display 30. The detector response for each of the twelve elements 21 is first multiplied by the appropriate gain coefficient and then by the appropriate weighting coefficient for the particular tristimulus value being calculated. The sum of these products is then scaled to correct for the $X_o$, $Y_o$, $Z_o$ perfect white under the specific illumination conditions employed. These tristimulus values can then be converted into the desired coordinant system, for example, L*, a*, and b* or L, C, and h.

EXAMPLE

Figure 13:
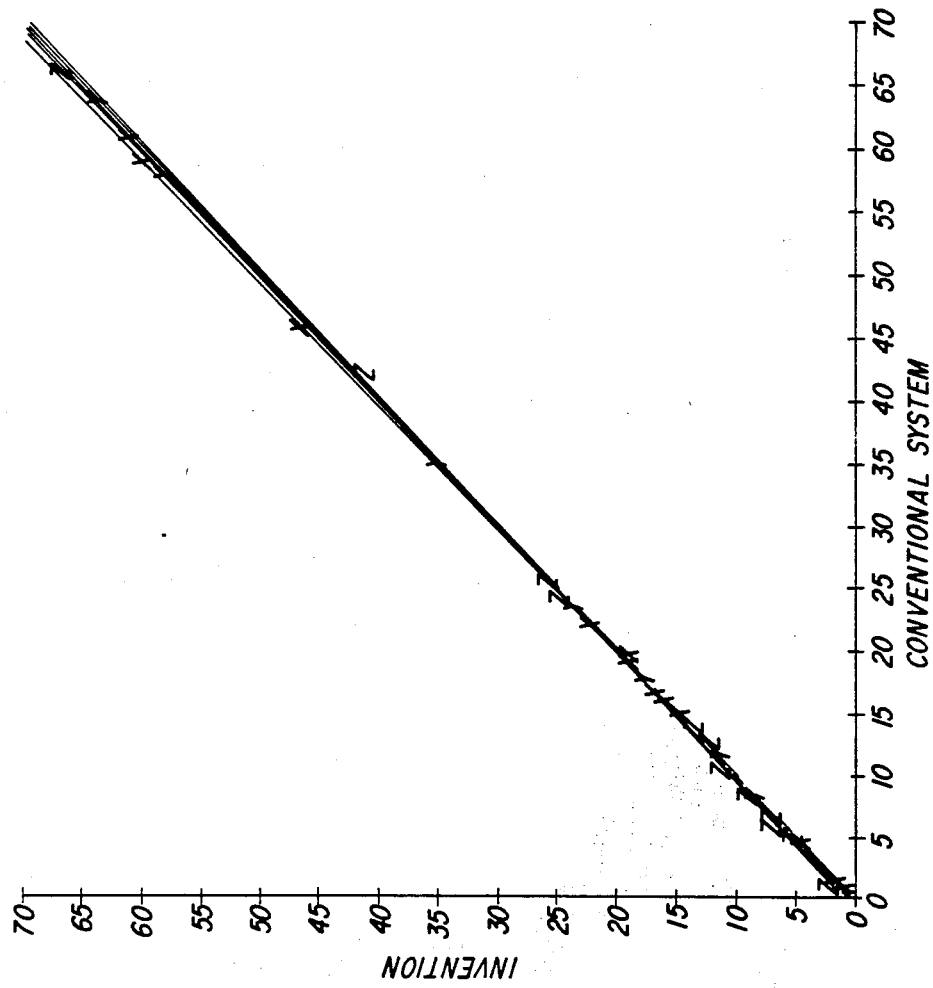
FIG. 13 is a comparison of the invention with the prior art.

FIG. 13 shows a comparison of tristimulus values X, Y, Z derived by the system of this invention versus the values obtained by a conventional laboratory spectrophotometric system.

The graph shows X, Y, Z color coordinates obtained for a set of twelve standard ceramic tiles, specifically Ceramic Colour Standards-Series II, as supplied by the British Ceramic Research Associated Ltd. For each tile, X, Y, Z, coordinates are obtained using first, the portable instrument of this invention and second, a conventional system. The values for the portable colorimeter of the invention are plotted along Y axis and the values for the prior art instrument are plotted along X axis. Linear least squares fitting of the X, Y, Z data show a slope of approximately 1 and low scatter about the line. The graph illustrates comparable performance of the two instruments.

The colorimeter of this invention can be used to characterize not only metallic paint films but any surface containing metallic particles, such as plastic containing reflective metallic flakes and also can be used on solid colors, i.e., colors not containing metallic particles. The method is particularly useful in shading paint wherein the L*, a* and b* values are determined for a standard. Then a batch of paint is manufactured according to a given formula; a painted panel of the batch is made and the L*, a* and b* values are determined. Often the batch of paint, even if carefully made, does not match the standard because of variations in pigments and color drift of pigment dispersions. The ΔL*, Δa* and Δb* values of the batch are calculated and if outside of an acceptable tolerance value, calculations are made for the addition of pigments in the form of mill bases and the mill bases added to the batch and a second panel prepared and values are measured as above. The process is repeated until there is an acceptance color match between the standard and the batch of paint.

While this invention has been described as having a preferred design, it will be understood that it is capable of further modification. This application, is therefore intended to cover any variations, uses or adaptations of the invention following the general principles thereof and including such departures from the present disclosure as come within known or customary practice in the art to which this invention pertains, and as may be applied to the essential features hereinbefore set forth and fall within the scope of this invention or the limits of the claims appended hereto.

I claim:

1. A portable colorimeter for determining the optical properties of a color film sample comprising:
    (a) an integrated unit housing irradiation means, detection means, control means, analysis means, and display means;
    (b) said irradiation means including a plurality of illumination means for sequentially illuminating the sample from a plurality of corresponding illuminating angles;
    (c) said detection means including an optical detector means for sequentially detecting the light reflected from the sample at a detection angle different from any of said illuminating angles;
    (d) whereby the light detected by said detector means is analyzed by said analysis means and converted into a signal displayed by said display means; and
    (e) said control means controlling said irradiation means, said detection means, said analysis means and said display means.

2. The colorimeter of claim 1 wherein:
three illumination means are used to illuminate the sample from three corresponding illuminating angles having values of about −35° to −20°, −10° to +10° and 20° to 75°, as measured from the sample normal.

3. The colorimeter of claim 2, wherein:
the three illumination means illuminate the sample from three corresponding illuminating angles having values of about −30°, 0°, and 65°, as measured from the sample normal.

4. The colorimeter of claim 1, wherein:
said detection angle having a value of about 35° to 55°, as measured from the sample normal.

5. The colorimeter of claim 4, wherein:
said detection angle having a value of about 45°, as measured from the sample normal.

6. The colorimeter of claim 1, wherein:
said optical detector means including an achromatic collection lens mounted at a distance of about twice its focal length from the sample, and a monochromator comprising a diffraction grating and an array of diode detectors; and
said monochromator is mounted opposite to the sample side of said lens.

7. The colorimeter of claim 6, wherein:
an entrance slit to said monochromator is mounted at a distance of about one focal length from said lens.

8. The colorimeter of claim 6 wherein:
said array of diode detectors including ten to sixteen detector elements.

9. The colorimeter of claim 1 wherein:
said irradiation means comprising three said illuminating means each with a filament and three corresponding lenses; and
each of said lenses is mounted at a distance of about one focal length from the filament of corresponding illuminating means.

10. The colorimeter of claim 1, further comprising:
an interface plate mounted over said irradiation means and said detection means; and
said interface plate including a center port for allowing the light to pass therethrough; and
means for releasably securing the colorimeter on the sample surface.

11. The colorimeter of claim 10, wherein:
said securing means comprising a plurality of magnetic feet positioned around said center port and protruding through said interface plate.

12. The colorimeter of claim 11, further comprising:
a generally donut-shaped flexible magnet means positioned concentrically with said center port for providing a light tight seal thereabout; and
a resilient sheet disposed between said interface plate and said flexible magnet means for protecting the sample surface.

13. The colorimeter of claim 10, wherein:
said irradiation means and said detection means being positioned in a semi-circle around said center port.

14. In a colorimeter having detector elements for determining the optical properties of a color film sample, a method of determining the tristimulus values from low resolution spectral reflectance data, comprising the steps of:
(a) determining for the illuminant a set of weighting coefficients for each tristimulus function curve $\bar{x}$, $\bar{y}$, and $\bar{z}$ by:
   (i) correcting the tristimulus function curve representing sensitivity data of the human eye by multiplying it with the spectral power distribution curve of the illuminant;
   (ii) determining the spectral response curve of the detector elements represented as a series of generally triangular pass bands; and
   (iii) and fitting the illuminant corrected tristimulus function curves with a multiple linear combination of the generally triangular pass bands representing the spectral response curve;
(b) illuminating the sample sequentially from a plurality of angles;
(c) detecting sequentially the light reflected from the sample at a detection angle different from any of said illuminating angles;
(d) determining sample reflectance response by a plurality of detector elements; and
(e) multiplying sample reflectance response of each detector element by corresponding weighting coefficient and adding them together to produce the tristimulus values for the color of the sample.

15. The method of claim 14, further comprising the step of:
calculating gain coefficients to adjust numerically the response of each detector element to be equal to the reflectance of a white calibration tile at an appropriate wavelength.

16. The method of claim 15, comprising:
multiplying sample reflectance response of each detector element first by corresponding gain coefficient and then by corresponding weighting coefficient; and
adding the data obtained above for all detector elements and scaling to correct for the tristimulus values ($X_o$, $Y_o$, $Z_o$) for perfect white color for the specific illumination conditions employed.

17. The method of claim 14, comprising:
illuminating the sample sequentially from three angles having values of about $-35°$ to $-20°$, $-10°$ to $+10°$ and $20°$ to $75°$, as measured from the sample normal.

18. The method of claim 17, comprising:
illuminating the sample sequentially from three angles having values of about $-30°$, $0°$ and $65°$, as measured from the sample normal.

19. The method of claim 14, comprising:
detecting sequentially the light reflected from the sample at said detection angle having a value of about $35°$ to $55°$ as measured from the sample normal.

20. The method of claim 19, comprising:
detecting sequentially the light reflected from the sample at said detection angle having a value of about $45°$, as measured from the sample normal.

21. The method of claim 14, comprising:
determining sample reflectance response by ten to sixteen detector elements.

* * * * *